(12) United States Patent
Korsgren et al.

(10) Patent No.: US 7,045,502 B2
(45) Date of Patent: May 16, 2006

(54) USE OF MELAGATRAN FOR THE MANUFACTURE OF A MEDICAMENT FOR THE TREATMENT OF TYPE 1 DIABETES MELLITUS

(75) Inventors: Olle Korsgren, Uppsala (SE); Bo Nilsson, Uppsala (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/502,069

(22) PCT Filed: Jan. 21, 2003

(86) PCT No.: PCT/SE03/00087

§ 371 (c)(1),
(2), (4) Date: Dec. 9, 2004

(87) PCT Pub. No.: WO03/061682

PCT Pub. Date: Jul. 31, 2003

(65) Prior Publication Data

US 2005/0090424 A1    Apr. 28, 2005

(30) Foreign Application Priority Data

Jan. 23, 2002  (SE)  .................................. 0200198

(51) Int. Cl.
*A01N 37/18*   (2006.01)
*A01N 63/00*   (2006.01)

(52) U.S. Cl. .......................... 514/2; 424/93.7
(58) Field of Classification Search ................ 530/300
See application file for complete search history.

(56) References Cited

U.S. PATENT DOCUMENTS 6,683,054 B1 *  1/2004  Kirk ............................. 514/18

FOREIGN PATENT DOCUMENTS

| WO | WO-94/29336 | 12/1994 |
|---|---|---|
| WO | WO-97/23499 | 7/1997 |
| WO | WO-00/41716 | 7/2000 |
| WO | WO-00/45837 | 8/2000 |
| WO | WO-02/36157 | 5/2002 |

OTHER PUBLICATIONS

Gustafsson D, et al., Throm Haemost., 1998, 79(1), pp. 110-118.*
Gustaffson, et al., 1998, Tromb Haemost, 79, 110-8.*
Shapiro AM., et al., N. Engl. J. Med., 2000, 343, 230-8.*
Bennet, W., et al., 1999, Diabetes, 48, 1907-14.*
Soria, et al., Diabetes, 2000, 49, 1-6.*
Shapiro, A.M. James, et al., "Islet Transplantation in Seven Patients with Type 1 Diabetes Mellitus Using a Glucocorticoid-Free Immunosuppressive Regimen," The New England Journal of Medicine, 343(4):220-238 (2000).
Ozmen, L., et al., "Inhibition of Thrombin Abrogates the Instant Blood-Mediated Inflammatory Reaction Triggered by Isolated Human Islets, Possible Application of the Thrombin Inhibitor Melagatran in Clinical Islet Transplantation," Diabetes, 51:1779-1784 (2002).
Boker, A., et al., "Human Islet Transplantation: Update," World J. Surg., 25:481-486 (2001).
Bennet, W., et al., "Incompatibility Between Human Blood and Isolated Islets of Langerhans, A Finding With Implications for Clinical Intraportal Islet Transplantation?" Diabetes, 48:1907-1914 (1999).
Sefton, M.V., et al., "Making microencapsulation work: conformal coating, immobilization gels and in vivo performance," Journal of Controlled Release, 65:173-186 (2000).
Hill, R.S., et al., "Immunoisolation of Adult Porcine Islets for the Treatment of Diabetes Mellitus, The Use of Photopolymerizable Polyethylene Glycol in the Conformal Coating of Mass-isolated Porcine Islets," Annals of the New York Academy of Sciences, 831:332-343.

* cited by examiner

*Primary Examiner*—Bruce R. Campell
*Assistant Examiner*—Satyanarayana R. Gudibande
(74) *Attorney, Agent, or Firm*—Fish & Neave IP Group Ropes & Gray LLP

(57) ABSTRACT

According to the invention there is provided the use of melagatran, or a pharmaceutically-acceptable derivative thereof, for the manufacture of a medicament for the treatment of Type I diabetes.

19 Claims, 2 Drawing Sheets

Figure 1:
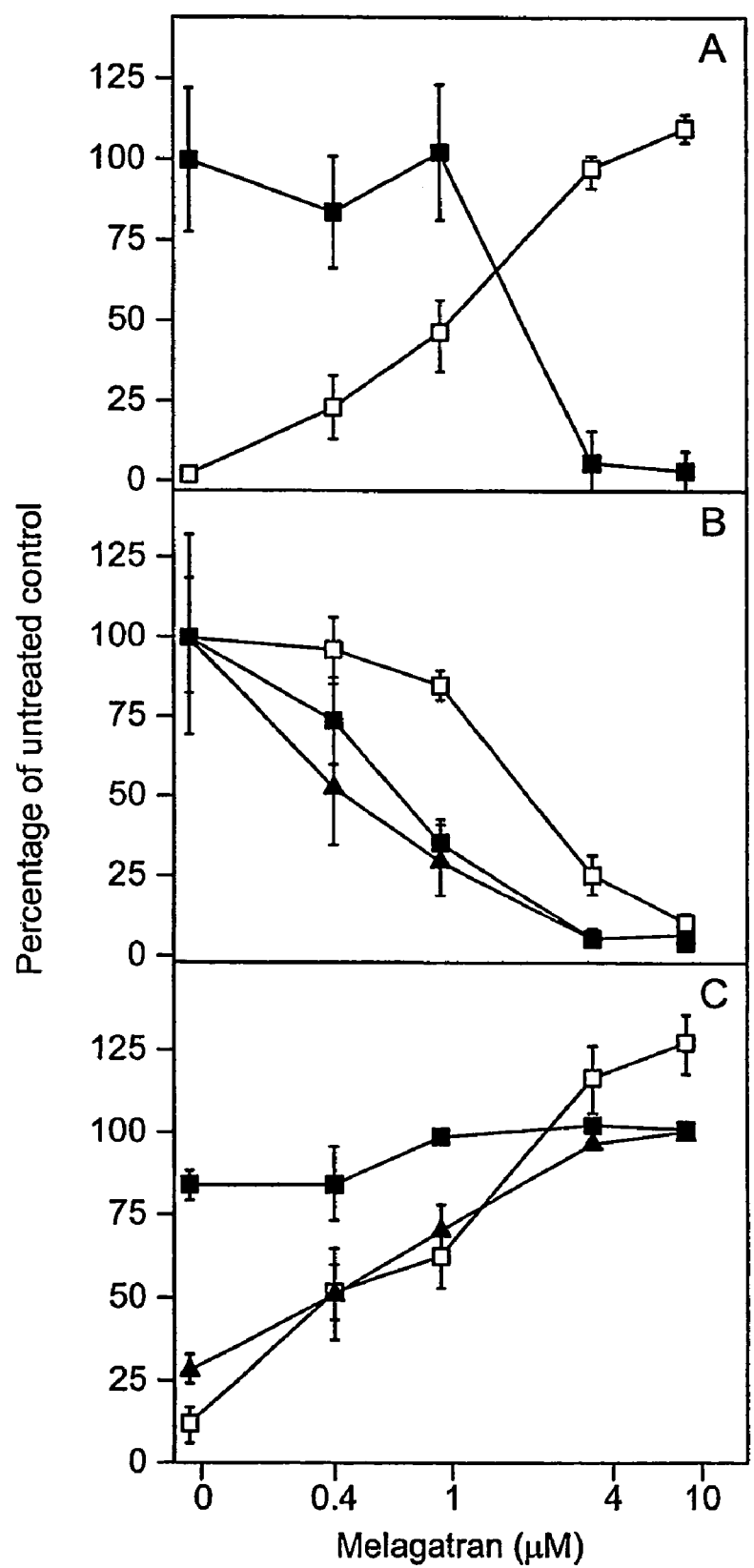

USE OF MELAGATRAN FOR THE MANUFACTURE OF A MEDICAMENT FOR THE TREATMENT OF TYPE 1 DIABETES MELLITUS

RELATED APPLICATIONS

This application is a national stage filing under 35 U.S.C. 371 of International Application PCT/SE03/00087, filed Jan. 21, 2003, which claims priority from Swedish Application No. 0200198-0, filed Jan. 23, 2002. International Application PCT/SE03/00087 was published under PCT Article 21(2) in English.

This invention relates to a new use of a low molecular weight thrombin inhibitor.

Combined kidney-pancreas transplantation has become a valid therapeutic option for the treatment of Type I (insulin-dependent) diabetes with end-stage diabetic nephropathy, in view of the fact that it restores metabolic control, improves quality of life and reduces the high mortality rate usually found in this group of patients.

80% of the patients subjected to kidney-pancreas transplantation are still alive after 10 years, in sharp contrast to the 20% survival rate of those receiving a kidney alone.

However, in view of the surgical risk that is involved, as well as the post-operative complications that often result, pancreas transplantation is typically only offered to patients with end-stage diabetic nephropathy.

In view of this lack of availability, an alternative method of potentially reducing insulin-dependency involving the transplantation of isolated islets of Langerhans has been developed.

Although several transplantation sites have been evaluated in experimental models, only intraportal transplantation has been established thus far for islet transplantation in the clinical setting.

Islet transplantation is easy to perform and safe, though for many years the clinical outcome was markedly inferior when compared to full pancreas transplantation, in that only 8% of patients were insulin-independent 1 year after transplantation, as opposed to about 70% with full kidney-pancreas transplantation. These poor results serve to demonstrate that only a small proportion of the islet mass proceeds to engraft effectively following this kind of transplantation.

A recent breakthrough discovery by Shapiro et al (*N. Engl. J. Med.*, 343, 230 (2000)) demonstrated that insulin independence could be far more readily obtained by treating the patient with repeated transplants of islets from more than one donor.

By way of investigation into possible reasons for the poor results observed in the case of single donor transplants, an in vitro islet perfusion system that mimics the situation in vivo immediately after transplantation of islet cells into the portal vein was devised (Bennet et al, *Diabetes*, 48, 1907 (1999)). This study demonstrated that exposure of human islets to ABO compatible blood in vitro induces a far-reaching series of inflammatory events, namely activation of the coagulation and complement systems, rapid binding and activation of platelets and binding of leukocytes, together resulting in disruption of islet integrity. Intraportal transplantation of allogeneic islets was shown to cause a similar chain of events in vivo in the pig.

The detrimental effects of this instant blood-mediated inflammatory reaction (IBMIR) could provide a explanation for the relatively low success rate of the islet transplantation procedure and/or the need of islets from several donors in order to obtain normoglycemia.

Bennet et al also reported that a combination of heparin and soluble recombinant CR1 (complement inhibitor), but, interestingly, not the individual substances alone, prevented most of the disruption of normal islet morphology and infiltration of the islets. Despite this preventative effect, a thin layer of platelets and fibrin could still be observed on the islet surface. See also international patent application WO 00/45837.

Hence there remains a clinical need for an effective means of increasing post-operative insulin-independence following treatment of Type I diabetic patients, e.g. by transplantation of islets of Langerhans, and particularly procedures involving single transplantations of islets from a single donor.

International patent application WO 94/29336 discloses a group of compounds that are useful as inhibitors of serine proteases, such as thrombin and/or kininogenases. The thrombin-inhibiting compounds are thus indicated as anti-coagulants, and the kininogenase-inhibiting compounds as anti-inflammatory agents. The use of the compounds in the treatment of diabetes and/or the transplantation of cells, such as islets of Langerhans, is neither disclosed nor suggested.

One of the thrombin-inhibiting compounds that is specifically disclosed in WO 94/29336 is HOOC—$CH_2$—(R) Cgl-Aze-Pab-H (wherein Cgl represents cyclohexylglycinyl, Aze represents (S)-azetidine-2-carboxyl, and Pab represents para-amidinobenzylamino), which is also known as melagatran (see Example 1 of WO 94/29336).

International Patent Application WO 97/23499 discloses prodrugs of inter alia melagatran. Again, the use of the compounds in the treatment of diabetes and/or the transplantation of cells, such as islets of Langerhans, is neither disclosed nor suggested.

International patent application, WO 00/41716 discloses the use of melagaftran and derivatives thereof in the treatment of inflammation. The use of melagatran in the treatment of IBMR, diabetes and/or the transplantation of cells, such as islets of Langerhans, is neither mentioned nor suggested.

We have now found that melagatran almost completely inhibits IBMIR, including complement activation and the activation and binding of platelets to islets of Langerhans, and that therefore melagatran and derivatives thereof are potentially useful in the treatment of diabetes.

According to a first aspect of the invention there is provided the use of melagatran, or a pharmaceutically-acceptable derivative thereof, for the manufacture of a medicament for the treatment of Type I diabetes mellitus.

The term "Type I diabetes mellitus" will be understood by those skilled in the art to include insulin-dependent diabetes (IDD).

Melagatran and derivatives thereof may find particular utility in treatments of Type I diabetes in which transplantation is involved. Such transplantation may involve kidney transplantation, pancreas transplantation or combined kidney-pancreas transplantation, but preferably involves transplantation of cells, such as insulin-producing cells or precursors thereof. Preferred insulin-producing cells include islets of Langerhans. Precursors of insulin-producing cells include pregenitors of such cells, such as stem cells, which may be injected into the pancreas using techniques known to those skilled in the art and thereafter develop into insulin-producing cells.

Thus, according to a further aspect of the invention there is provided the use of melagatran, or a pharmaceutically-acceptable derivative thereof, for the manufacture of a medicament for use in a method of transplantation of cells, including insulin-producing cells or precursors thereof, such as islets of Langerhans or stem cells.

Preferred islets of Langerhans include beta cells (i.e. pancreatic insulin-producing cells) but the use according to the invention is not restricted to the transplantation of such cells. Transplantation may involve isolated or multiple procedures and cells may be obtained for use in such (a) procedure(s) from one or more donors. Preferred procedures may involve single transplantation from a single donor.

We have found that melagatran and derivatives thereof may enhance the engraftment of islets of Langerhans in the liver following transplantation (such as intraportal transplantation), when compared to engraftment following transplantation in the absence of melagatran/derivatives.

There is thus provided the use of melagatran, or a pharmaceutically-acceptable derivative thereof, for the manufacture of a medicament for use in a method of:

(a) engraftment of islets of Langerhans, for example in the liver; and
(b) improving insulin-independency (e.g. achieving normoglycemia) in patients having Type I diabetes.

There is further provided the use of melagatran, or a pharmaceutically-acceptable derivative thereof, for the manufacture of a medicament for the treatment of IBMIR.

The term "IBMIR" (instant blood-mediated inflammatory reaction) when used in this context includes the series of inflammatory events that is known to occur following transplantation of islets of Langerhans into the portal vein, namely activation of the coagulation and complement systems, as well as rapid binding and activation of platelets and binding of leukocytes, which events may lead to a disruption of islet integrity.

For the avoidance of doubt, the term "treatment" includes both therapeutic and prophylactic treatment. By prophylactic treatment, we include prevention (inhibition) of the progress of, for example, IBMIR "Pharmaceutically-acceptable derivatives" of melagatran includes salts (e.g. pharmaceutically-acceptable non-toxic organic or inorganic acid addition salts) and solvates. It will be appreciated that the term further includes derivatives that have, or provide for, the same biological function and/or activity as melagatran. Thus, for the purposes of this invention, the term also includes prodrugs of melagatran. "Prodrugs" of melagatran include any composition of matter that, following oral or parenteral administration, is metabolised in vivo to form melagatran in an experimentally-detectable amount, and within a predetermined time (e.g. within a dosing interval of between 6 and 24 hours (i.e. once to four times daily)). For the avoidance of doubt, the term "parenteral" administration includes all forms of administration other than oral administration.

Prodrugs of melagatran that may be mentioned include those disclosed in international patent application WO 97/23499. Preferred prodrugs are those of the formula $R^1O_2C$—$CH_2$—(R)Cgl-Aze-Pab-OH (see the list of abbreviations above or in WO 97/23499), wherein $R^1$ represents $C_{1-10}$ alkyl or benzyl, such as linear or branched $C_{1-6}$ alkyl (e.g. $C_{1-4}$ alkyl, especially methyl, n-propyl, i-propyl, t-butyl and, particularly, ethyl) and the OH group replaces one of the amidino hydrogens in Pab.

In accordance with the invention, melagatran and derivatives thereof may be administered orally, intraportally, intravenously, subcutaneously, buccally, rectally, dermally, nasally, tracheally, bronchially, topically, by any other parenteral route or via inhalation.

Melagatran and derivatives thereof may be administered in the form of a pharmaceutical preparation comprising melagatran in a pharmaceutically-acceptable dosage form. Depending on the patient to be treated, as well as the route of administration, such compositions may be administered at varying doses.

Preferred modes of delivery are systemic. For melagatran and derivatives thereof, preferred modes of administration are parenteral (more preferably intravenous, and especially intraportal) or oral. Such modes of administration may be found to provide for maximisation of the concentration of melagatran/derivative in the liver following administration.

In the treatment of Type I diabetes, melagatran and derivatives thereof are preferably co-administered along with islets of Langerhans in an islet transplantation process.

According to a still further aspect of the invention there is provided a kit of parts comprising components:

(a) a first component comprising melagatran or a pharmaceutically-acceptable derivative thereof; and
(b) a second component comprising cells, for example insulin-producing cells or precursors thereof, such as islets of Langerhans or stem cells, which components (a) and (b) are each provided in a form that is suitable for administration in conjunction with the other, and are also suitable for sequential, separate and/or simultaneous use in the treatment of Type I diabetes and/or a method of cell transplantation.

Components (a) and (b) may thus be provided in the form of (as appropriate) melagatran/derivative, or cells, along with a pharmaceutically-acceptable adjuvant, diluent or carrier.

According to a further aspect of the invention, there is provided a method of making a kit of parts as defined above, which method comprises bringing a component (a), as defined above, into association with a component (b), as defined above, thus rendering the two components suitable for administration in conjunction with each other.

Thus, there is further provided a kit of parts comprising:
(I) one of components (a) and (b) as defined herein; together with
(II) instructions to use that component in conjunction with the other of the two components.

With respect to the kits of parts as described herein, by "administration in conjunction with", we include that respective components (a) and (b) are administered, sequentially, separately and/or simultaneously, over the course of treatment Further, the term "in conjunction with" includes that one or other of the two components (a) and (b) may be administered prior to, after, and/or at the same time as, administration with the other component. When used in this context, the terms "administered simultaneously" and "administered at the same time as" include that the two components are administered within 48 hours (e.g. 24 hours) of each other.

When separate components are administered, the sequence in which they may be administered (i.e. whether, and at what point, sequential, separate and/or simultaneous administration takes place) may be determined by the physician or skilled person.

In the therapeutic treatment of mammals, and especially humans, melagatran/derivatives will be administered as pharmaceutical formulations in admixture with pharmaceutically-acceptable adjuvants, diluents or carriers, which may be selected with due regard to the intended route of administration and standard pharmaceutical practice.

Suitable formulations for use in administering melagatran and derivatives (including prodrugs) thereof are described in the literature, for example as described in inter alia international patent applications WO 94/29336, WO 96/14084, WO 96/16671, WO 97/23499, WO 97/39770, WO 97/45138, WO 98/16252, WO 99/27912, WO 99/27913, WO 00/12043 and WO 00/13671, the disclosures in which documents are hereby incorporated by reference. Otherwise, the preparation of suitable formulations may be achieved non-inventively by the skilled person using routine techniques.

According to a further aspect of the invention there is provided a pharmaceutical formulation for use in the treatment of Type I diabetes comprising an effective amount of melagatran, or a pharmaceutically-acceptable derivative thereof, in admixture with a pharmaceutically-acceptable adjuvant, diluent or carrier.

The amounts of melagatran/derivative in the respective formulation will depend on the severity of the condition, and on the patient, to be treated, as well as the compound(s) which is/are employed, but may be determined non-inventively by the skilled person.

Suitable doses of melagatran/derivatives in the treatment of mammalian, especially human, patients may be determined routinely by the medical practitioner or other skilled person, and include the respective doses discussed in the prior art documents that are mentioned hereinbefore, the relevant disclosures in which documents are hereby incorporated by reference.

In the case of melagatran, suitable doses of active compound, prodrugs and derivatives thereof in the therapeutic and/or prophylactic treatment of mammalian, especially human, patients include those which give a mean plasma concentration of up to 5 µmol/L, for example in the range 0.001 to 5 µmol/L over the course of treatment of the relevant condition. Suitable doses may thus be in the range 0.1 mg once daily to 25 mg three times daily, and/or up to 100 mg infused parenterally over a 24 hour period, for melagatran, and in the range 0.1 mg once daily to 100 mg three times daily for prodrugs of melagatran including those specifically mentioned hereinbefore.

In any event, the physician, or the skilled person, will be able to determine the actual dose which will be most suitable for an individual patient which is likely to vary with the age, weight, sex and response of the particular patient to be treated. The above-mentioned dosages are exemplary of the average case; there can, of course, be individual instances where higher or lower dosage ranges are merited, and such are within the scope of this invention.

Transplantation of islets of Langerhans may be achieved by way of routine techniques, for example, by suspending them in an appropriate buffer, followed by injection and/or infusion of such a suspension into the portal vein via a transhepatic syringe or a catheter, or as described in by Boker et al in *World J. Surg.*, 25, 481 (2001) (the relevant disclosure in which document is hereby incorporated by reference), or as described hereinafter.

According to a further aspect of the invention there is provided a method of treating Type I diabetes, which comprises administering a therapeutically-effective amount of melagatran, or a pharmaceutically-acceptable derivative thereof, to a patient in need of such treatment.

The uses and methods described herein may have the advantage that, in the treatment of Type I diabetes, and in particular in the alleviation of insulin dependence in patients with Type I diabetes by way of transplantation of islets of Langerhans, melagatran and derivatives thereof may not possess disadvantages of known therapies.

The invention is illustrated, but in no way limited, by the following example, in which:

FIG. 1 illustrates changes in various biological markers in human islets incubated in the tubing loop model filled with ABO-compatible blood containing melagatran at concentrations ranging from 0 to 10 µM. Panel A illustrates changes in platelet particle count (white squares) and the release of β-TG (black squares). Panel B illustrates changes in prothrombin fragment 1+2 (white squares), TAT (black squares) and FXIa-AT (black triangles). Panel C illustrates changes in lymphocyte (black squares), monocyte (white squares) and PMN (black triangles) particle counts. The values represent data minus the medium control (no islets or melagatran) after 60 minutes and are expressed as percentage of the values for the untreated control containing human islets but no melagatran.

Figure 2:
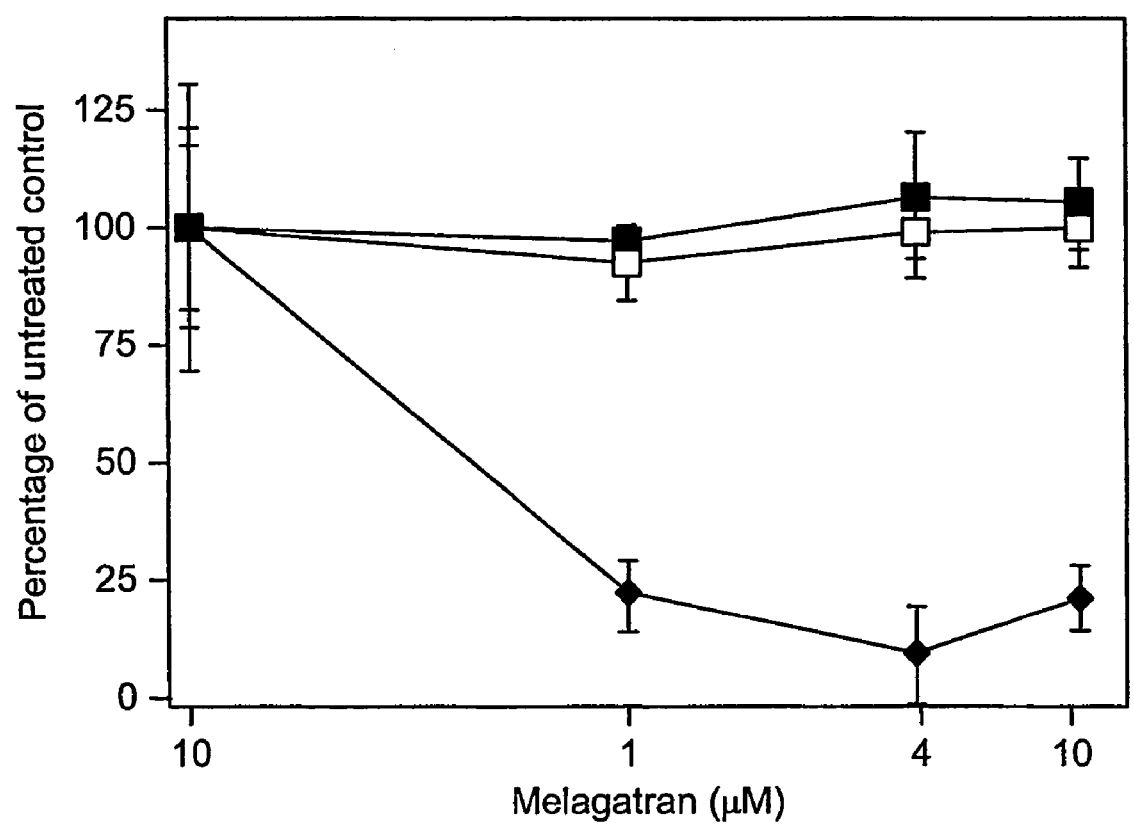

FIG. 2 illustrates changes in the generation of soluble C3a (white squares) and bound C3 fragments (black squares) in a serum model with no islets present, and changes in soluble C3a (black diamonds) in the tubing loop model containing islets in ABO-compatible blood with melagatran at concentrations of 0 to 10 µM.

EXAMPLE

Effect of Melagatran on IBMIR

Materials and Methods

Islet Isolation

Pancreases were obtained from cadaver donors after consent was obtained either from the organ donor registry or from relatives. The organs were obtained from three female and two male normoglycemic donors (aged 59–85 years, three with blood group 0 and two with blood group A). The islets were isolated at the Division for Clinical Immunology at the University of Uppsala using a modification of previously described semiautomated digestion-filtration methods (Brandhorst et al, *Cell Transplant.*, 7, 489 (1998) and Ricordi et al, *Diabetes*, 37, 413 (1988)). This isolation procedure was followed by further purification on a continuous density gradient in a refrigerated COBE 2991 centrifuge (COBE Blood Component Technology, Lakewood, Colo., USA). The islets were placed in untreated culture flasks and maintained in suspension culture at 37° C. (5% $CO_2$) for. 1 to 5 days. The culture medium (CMRL 1066; ICN Biomedicals, Costa Mesa, Calif.) was changed every other day. The volume and purity of the islets were determined by microscopic sizing on a grid after staining with diphenylthiocarbazone. The purity of the islet preparations used in this study ranged from 40% and 95% (70±6.3%) (amount of endocrine compared to exocrine/duct tissue in the preparation; mean ±SD). Viability was assessed in terms of insulin secretion in response to a glucose challenge in a dynamic perfusion system (in 1.67 mmol/L glucose, then in 16.7 mmol/L, and finally back to 1.67 mmol/L).

Heparin Treatment

All materials that came in contact with whole blood were furnished with a Corline heparin surface (Corline, Uppsala, Sweden) according to the manufacturer's recommendation (see *J. Clin. Immunol.*, 16, 222 (1996)). The surface concentration of heparin was 0.5 µg/cm$^2$, corresponding to approximately 0.1 U/cm$^2$, with an antithrombin binding capacity of 2–4 pmol/cm$^2$.

Preparation of Blood

Fresh human blood, obtained from healthy volunteers who had received no medication for at least 14 days, was collected in surface-heparinized 60-mL syringes (18 gauge, Microlance; Becton Dickinson, Franklin Lakes, N.J.). The cannulae of the syringes were connected to surface-heparinized-silicon tubing. During sampling, the syringes were rotated continuously.

Tubing Loops as a Model

A modification of the model previously described was used (see Bennet et al, *Diabetes*, 48, 1907 (1999), Gong et al, *J. Clin. Immunol.*, 16, 222 (1996) and Larsson et al, *Immunophamnacology*, 38, 119 (1997)). This device consisted of loops made of PVC (diameter, 6.3 mm; length, 390 mm) whose inner surface was furnished with immobilized heparin. The tubing was held together with a specially designed heparinized connector. A circular loop was formed when the ends of the connector were tightly pushed into the lumen of the tubing ends. A rocking apparatus, placed in a 37° C. incubator, was used to generate blood flow inside the loops. The loops were rocked at a setting that prevented the blood from coming into contact with the connectors. Up to twelve devices could be rocked at the same time. Ten 60-min islet experiments were performed, with islets isolated from five different donors. Melagatran (Astraeneca R&D Mölndal, Sweden), dissolved in 5 mM citrate buffer containing 0.15 M NaCl, pH 5.5, was tested at 0, 0.4 µM, 1 µM, 4 µM, and 10 µM. For each experiment, two loops of fresh human blood without islets, one containing CMRL 1066 (GibcoRBL, USA) and one containing 10 µM melagatran, were included as controls. Fresh ABO-compatible human blood from the same donor (5 mL) was added to each loop. The loops were placed on the rocking device for a 10-min preincubation with melagatran or citrate buffer. Thereafter, the loops were opened, and 150 µL of CMRL 1066, with or without 4 µL of islets (approximately 4,000 IEQ), was added to the loops, followed by another 60-min incubation on the rocking device at 37° C. Blood glucose levels were measured with a glucometer (Glucometer Elite; Bayer Diagnostics, Leverkusen, Germany) before the perfusion. After every perfusion the loop contents were filtered through 70 µm-diameter filters (Filcons, Cuptype; DAKO, Denmark). Both macroscopic blood clots and tissue recovered on the filters were frozen in liquid nitrogen for immunohistochemical staining. For immunohistochemical comparison, non-perfused islets were also frozen and stained by the same procedure. The remaining filtered blood was collected in 4.1 mM EDTA (final concentration) and used for hematologic analysis (platelets, lymphocytes, monocytes, and granulocytes) and assays of coagulation activation (prothrombin fragments 1+2, thrombin-antithrombin [TAT] and factor XIa-antithrombin complexes [FXIa-AT]), complement activation (C3a and sC5b-9), platelet activation (β-thromboglobulin [β-TG]), and insulin. Samples taken at 0 min were also included. In these samples, the blood was lo not added to the tubing loop but was instead transferred immediately to the EDTA-containing tubes. The blood samples were centrifuged at 4° C. at 3290×g for 20 minutes, and the plasma was collected and stored at −70° C. prior to analysis.

Activation of Complement in Wells of Microtiter Plates

The direct effect of melagatran on the complement system was studied using a method in which serum was incubated in the wells of microtiter plates (Nilsson et al, *Mol. Immunol.*, 30, 211 (1993)). Serum (100 µL) was added to each well of a 96-well microtiter plate together with melagatran at a final concentration of 0, 0.4, 1, 4, or 10 µM. After a 30-min incubation at 37° C., the serum was transferred to tubes containing EDTA (final concentration, 10 mM). These samples were stored at −70° C. before analysis of the complement fragment C3a (see below). In order to detect bound C3 fragments, the wells of the microtiter plates were washed with PBS containing 0.05% (v/v) TWEEN 20 and incubated with 100 µL of horseradish peroxidase (HRP)-conjugated anti-C3c (DAKO. AS, Glostrup, Denmark) for 60 min at 37° C. The binding of antibody was detected by the addition of 1,2-phenylendiamine dihydrochloride (Fluka, Switzerland), and the staining was monitored at 492 nm.

Blood and Plasma Analysis

Platelet counts and differential leukocyte counts were analyzed on a Coulter ACT-diff analyzer (Beckmnan Coulter, FL, USA) using EDTA-treated blood.

Enzyme Immunoassays (EIA)

A. Prothrombin Fragment 1+2 and Thrombin-Antithrombin (TAT)

Plasma levels of prothrombin fragment 1+2 and TAT were quantified using commercially available EIA kits (Enzygnost Prothrombin, fragments 1+2; TAT, Behringswerke, Marburg, Germany). The values are given as nmol/L and µg/L, respectively.

B. Factor XIa-Antithrombin (FXIa-AT)

Complexes between FXIa and AT were measured in plasma according to the method of Sanchez et al, *Thromb. Res.*, 89, 41 (1998). Values are expressed as µmol/L.

C. β-Thromboglobulin (β-TG)

β-TG was analyzed in EDTA-plasma using Asserachom (Diagnostica Stago, Asnières-sur-Seine, France). The values are expressed as IU/mL.

D. C3a

EDTA-plasma was analyzed as previously described (Nilsson Ekdahl et al, *Scand. J. Immunol.*, 35, 85 (1992)). Monoclonal antibody 4SD17.3 was used as capture antibody. Bound C3a was detected with biotinylated polyclonal anti-C3a followed by HRP-conjugated streptavidin (Amersham, Buckinghamshire, UK). Zymosan-activated serum, calibrated against a solution of purified C3a, served as a standard, and the values are given as ng/mL.

E. sC5b-9

Plasma was analyzed using a modification of the EIA described by Mollnes et al (see *Scand. J. Immunol.*, 35, 85 (1992) and *Artif. Organs*, 19, 909 (1995)). EDTA-plasma was added to microtiter plates coated with mAb anti-neoC9. sC5b-9 was detected by polyclonal anti-C5 antibodies (DAKO), followed by HRP-conjugated anti-rabbit immunoglobulin (DAKO). Zymosan-activated serum, defined as containing 40,000 arbitrary units (AU/mL), served as the standard. The values are given as AU/mL.

F. Insulin

Plasma concentrations of insulin were analyzed before and after islet perfusion with a commercial EIA kit (DAKO). Values are given as pmol/L.

Immunohistochemical Staining

Islets and macroscopic clots recovered on filters after perfusion with blood and various concentrations of melagatran were collected in an embedding medium (Tissue-Tek; Miles, Eckihart, Ind., USA) and snap-frozen in liquid nitrogen. Islets were sectioned and subsequently stained with HRP-conjugated mouse anti-human CD41a (R&D Systems, Abingdon, UK) and anti-CD11b (Clone 2LPM 19c, DAKO).

Statistical Analysis

Because of individual variation in blood cell counts and in plasma parameters, the changes were either calculated as a percentage of the values obtained in the medium control loop (for blood cells) or as a ratio of the values obtained in the experimental loop and in the islet loop with no melagatran. All results are expressed as mean ±SEM. Mean values were compared using Friedman ANOVA (Analyse-It, version 1.44, Software Ltd, UK). The significance was determined at $\alpha=0.05$. The data presented in FIGS. 1B, C and 2 represent the net values after subtraction of the data for the 0-min samples.

Results

Islet Function is not Affected by Melagatran

To confirm that melagatran had no adverse effect on islet function, we tested this inhibitor at the highest concentration used in the loop experiments (10 μM) in an islet perfusion system. Perfusion of islets with 10 μM melagatran did not induce insulin release, and subsequent glucose stimulation (16.7 mmol/L) was also normal.

Perfusion of Human Islets with Fresh Human ABO-Compatible Blood in the Tubing Loop Model With reference to Table 1. Glucose concentrations in the blood before islet perfusion ranged from 4.5–7.4 mmol/L. After a 60-min incubation of fresh non-anticoagulated human blood without islets in the control tubing loops, a slight drop was seen in the blood cell counts when compared with the 0-min samples. In addition, increases (3- to nearly 50-fold) in the coagulation (TAT, prothrombin fragment 1+2, and FXIa-AT), platelet (β-TG), and complement (C3a and sC5b-9) parameters were also seen. All of these alterations, however, were in absolute values small and considered to be normal background changes resulting from interactions of the blood with the tubing surface and the fluid-air interphase. In tubing loops without melagatran, nearly all the platelets were consumed after 60 min., concurrently with a pronounced secretion of β-TG. Granulocytes and monocytes were also consumed after 60 min, while lymphocytes were essentially unaffected. In addition, in the absence of melagatran, macroscopic clotting was seen and was accompanied by a significant rise in TAT, prothrombin fragment 1+2, and FXIa-AT complex levels. Marked increases in the complement activation product C3a and in plasma insulin levels were also observed, also sC5b-9 increased but to a lesser extent.

Melagatran Inhibits IBMIR in a Dose-Dependent Way

Melagatran diminished cell consumption and cascade system activation in a dose-dependent manner (Table 1; FIG. 1A-C). An effect on most parameters was observed already at concentrations as low as 0.4 μM. The cell counts were fully restored at $\geq 4$ μM (FIGS. 1A, 1C). The release of β-TG was also normalized at the same dosage (FIG. 1A). The coagulation parameters TAT and FXIa-AT decreased to nearly the same level as the medium control at 4 μM melagatran, but inhibition of prothrombin fragment 1+2 formation required higher doses of melagatran (FIG. 1B). In parallel with the FXIa-AT and TAT complexes, the complement activation product C3a was also inhibited by melagatran (FIG. 2). In order to investigate whether melagatran had any direct effect on the complement system, its effects were tested in human serum in which complement was activated on the polystyrene surface of microtiter plate wells (FIG. 2). Melagatran had no effect on the binding of C3 fragments to the polystyrene surface or on the generation of C3a, indicating that it does not directly affect the complement serine proteases.

Immunohistochemical Staining of Human Islets After Perfusion in the Tubing Loop Model After 60 min of perfusion the islets were consistently found to be embedded in clots. Immunohistochemical staining with anti-CD41a monoclonal antibody showed a capsule of fibrin and platelets surrounding the islets. In addition, there was an accumulation of CD 11b$^+$ PMN and monocytes in the thrombi, many of which were seen to penetrate into the islets. In contrast, islets that had been incubated with fresh human blood in the presence of 10 μM melagatran showed no signs of clot formation. There were almost no CD41$^+$ platelets surrounding the islet surface, and only a few CD11b$^+$ cells were found to have penetrated into the islets. No CD41$^+$ or CD11b$^+$ staining was observed in control islets that had not been exposed to blood.

These results demonstrate that melagatran abrogated IBMIR in vitro and is therefore potentially of use in the transplantation of islets of Langerhans and thus in the treatment of diabetes.

TABLE 1

Blood cell counts, coagulation and complement parameters before and after 60 min of human islet perifusion with fresh ABO-compatible blood

|  | 0 min | 60 min | | |
|---|---|---|---|---|
|  |  |  | Islets | |
|  | No islets* | No islets* | No melagatran | 10 μM melagatran |
| n | 10 | 10 | 10 | 10 |
| Platelets (×10$^9$/L) | 240 ± 11 | 160 ± 7.6 | 2.4 ± 1.1$^\dagger$ | 170 ± 8.2$^\ddagger$ |
| Lymphocytes (×10$^9$/L) | 2.2 ± 0.1 | 2.0 ± 0.1 | 1.7 ± 0.1 | 2.0 ± 0.1$^\ddagger$ |
| Monocytes (×10$^9$/L) | 0.4 ± 0.0 | 0.5 ± 0.1 | 0.1 ± 0.0$^\dagger$ | 0.6 ± 0.1$^\ddagger$ |
| Granulocytes (×10$^9$/L) | 4.0 ± 0.3 | 3.8 ± 0.3 | 1.0 ± 0.1$^\dagger$ | 3.7 ± 0.3$^\ddagger$ |
| TAT (μg/mL) | 9.4 ± 2.2 | 470 ± 87 | 16000 ± 2900$^\dagger$ | 890 ± 160$^\ddagger$ |
| Prothrombin F1 + 2 (nmol/L) | 1.5 ± 0.2 | 25 ± 5.1 | 1000 ± 180$^\dagger$ | 110 ± 28$^\ddagger$ |
| FXIa-AT (μmol/L) | 0.02 ± 0.0 | 0.4 ± 0.1 | 14 ± 2.6$^\dagger$ | 0.9 ± 0.6$^\ddagger$ |
| β-TG (IU/mL) | 520 ± 130 | 1300 ± 180 | 4000 ± 450 | 1300 ± 200$^\ddagger$ |
| C3a (ng/mL) | 120 ± 15 | 530 ± 62 | 950 ± 140$^\dagger$ | 510 ± 50$^\ddagger$ |
| sC5b-9 (AU/mL) | 24 ± 3.4 | 130 ± 16 | 180 ± 31 | 140 ± 17.0 |
| Insulin (mU/L) | 12 ± 4.3 | 10 ± 4.0 | 460 ± 140$^\dagger$ | 1500 ± 350$^\ddagger$ |

*Control containing blood and medium, but no islets
$^\dagger$Significant difference when compared to the control loop after 60 min of perfusion
$^\ddagger$Significant difference when compared to the islet loops with no melagatran

The invention claimed is:

1. A method of transplantation of cells, which method comprises the administration of a therapeutically-effective amount of melagatran, or a pharmaceutically-acceptable derivative thereof, to a patient about to be, being, or having been, subjected to such transplantation.

2. A method as claimed in claim 1, wherein the cells are insulin-producing cells or precursors thereof.

3. A method as claimed in claim 1, wherein the cells are islets of Langerhans.

4. A method as claimed in claim 1, wherein the cells are precursors of insulin-producing cells which are stem cells.

5. A method as claimed in any one of claims 1 to 3, wherein the derivative of melagatran is a prodrug of melagatran.

6. A method as claimed in any one of claims 1 to 3, wherein the derivative of melagatran is a prodrug of the formula $R^1O_2C$—$CH_2$—(R)Cgl-Aze-Pab-OH, wherein $R^1$ represents linear or branched $C_{1-6}$ alkyl and the OH group replaces one of the amidino hydrogens in Pab.

7. A method as claimed in claim 6, wherein $R^1$ represents methyl, ethyl, n-propyl, i-propyl or t-butyl.

8. A method as claimed in claim 6, wherein $R^1$ represents ethyl.

9. A method of engrafting islets of Langerhans, which method comprises administering a therapeutically-effective amount of melagatran, or a pharmaceutically-acceptable derivative thereof, to a patient about to be, being, or having been, subjected to transplantation of such islets.

10. A method as claimed in claim 9, wherein the islets engraft in the liver.

11. A method as claimed in claims 9 or claim 10, wherein the derivative of melagatran is a prodrug of melagatran.

12. A method as claimed in claims 9 or claim 10, wherein the derivative of melagatran is a prodrug of the formula $R^1O_2C$—$CH_2$—(R)Cgl-Aze-Pab-OH, wherein $R^1$ represents linear or branched $C_{1-6}$ alkyl and the OH group replaces one of the amidino hydrogens in Pab.

13. A method as claimed in claim 12, wherein $R^1$ represents methyl, ethyl, n-propyl, i-propyl or t-butyl.

14. A method as claimed in claim 12, wherein $R^1$ represents ethyl.

15. A method of treatment of instant blood-mediated inflammatory reaction, which method comprises administering a therapeutically-effective amount of melagatran, or a pharmaceutically-acceptable derivative thereof, to a patient in need of such treatment.

16. A method as claimed in claim 15, wherein the derivative of melagatran is a prodrug of melagatran.

17. A method as claimed in claim 15, wherein the derivative of melagatran is a prodrug of the formula $R^1O_2C$—$CH_2$—(R)Cgl-Aze-Pab-OH, wherein $R^1$ represents linear or branched $C_{1-6}$ alkyl and the OH group replaces one of the amidino hydrogens in Pab.

18. A method as claimed in claim 15, wherein $R^1$ represents methyl, ethyl, n-propyl, i-propyl or t-butyl.

19. A method as claimed in claim 16, wherein $R^1$ represents ethyl.

* * * * *